United States Patent
Lei et al.

(10) Patent No.: US 7,064,227 B1
(45) Date of Patent: Jun. 20, 2006

(54) PRECURSORS FOR SILICA OR METAL SILICATE FILMS

(75) Inventors: Xinjian Lei, Vista, CA (US); Ron Rulkens, Milpitas, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 39 days.

(21) Appl. No.: 11/008,069

(22) Filed: Dec. 9, 2004

(51) Int. Cl.
*C07F 7/02* (2006.01)

(52) U.S. Cl. ...................... 556/463; 556/400

(58) Field of Classification Search ............. 556/463, 556/400
See application file for complete search history.

(56) References Cited

FOREIGN PATENT DOCUMENTS

| WO | WO 02/27063 | 4/2002 |
|----|-------------|--------|
| WO | WO 03/083167 | 10/2003 |

OTHER PUBLICATIONS

Backer, et al, Esters Mixtes de L'Acide Tetrathio-Orthosilicique, Rec. Trav. Chim., 61, 1942, pp. 500-512.
Goedel, et al, Hyperbranched Poly(alkoxysilonanes), Polymer Preprints, 42(1), 2001, pp. 242-243.
Hausman, et al, Rapid Vapor Deposition of Highly Conformal Silica Nanoaluminates, Sci., vol. 298, 2002, pp. 402-406.
Muller, et al, Zur Darstellung von Alkoxy-und Alkoxysiloxy-silanolen, Z. Chem., 23, Jg. 1983, p. 252.
Schott, et al, Alkoxy-silanole-partielle Kieselsaureester, Z. Anorg. Allg. Chemie, 459, 1979, pp. 177-186.

*Primary Examiner*—Elvis O. Price
(74) *Attorney, Agent, or Firm*—Geoffrey L. Chase

(57) ABSTRACT

A composition selected from the group consisting of bis(tert-butoxy)(isopropoxy)silanol, bis(isopropoxy)(tert-butoxy)silanol, bis(tert-pentoxy)(isopropoxy)silanol, bis(isopropoxy)(tert-pentoxy)silanol, bis(tert-pentoxy)(tert-butoxy)silanol, bis(tert-butoxy)(tert-pentoxy)silanol and mixtures thereof; its use to form a metal or metalloid silicate layer on a substrate and the synthesis of the mixed alkoxysilanols.

14 Claims, 1 Drawing Sheet

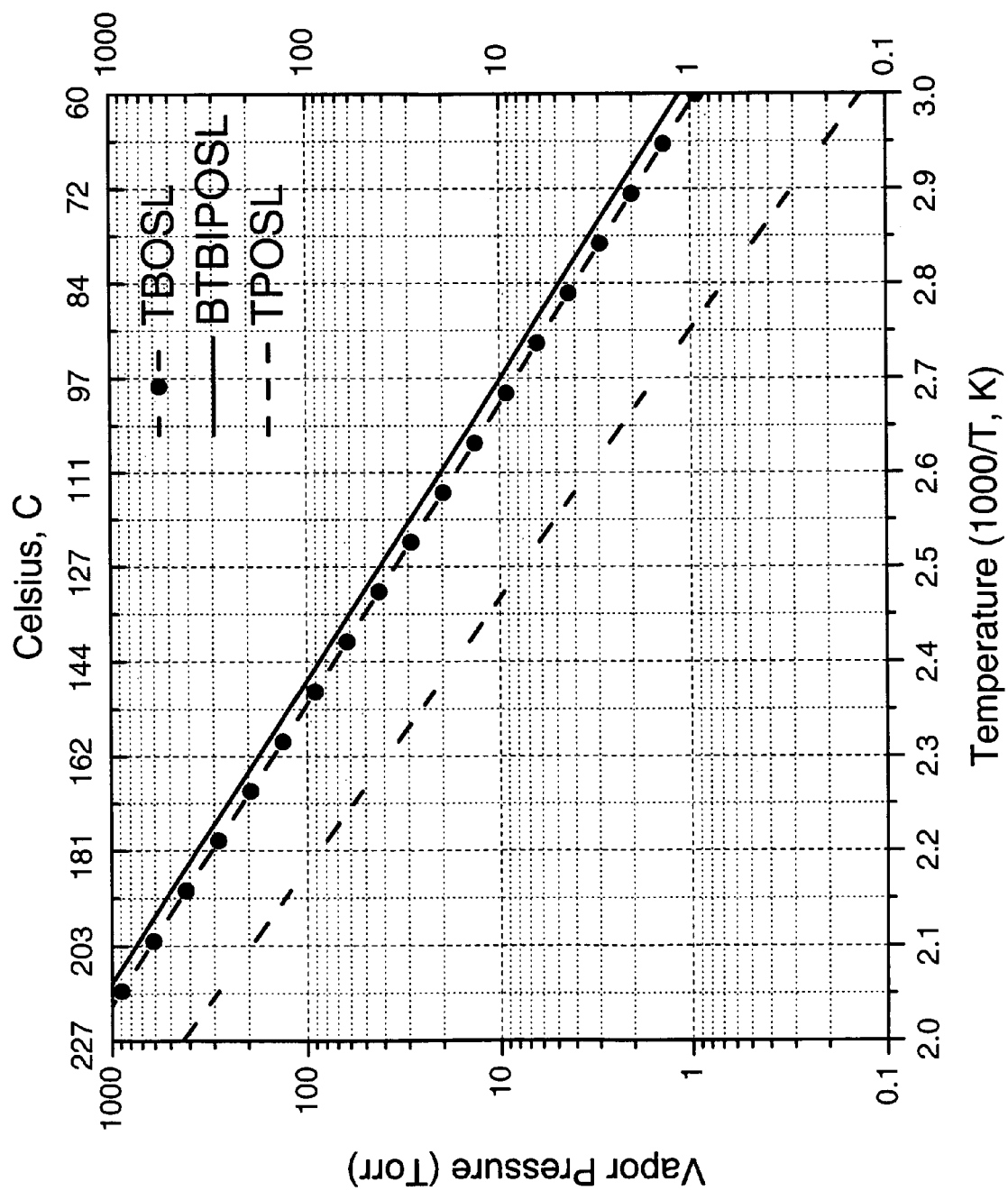

PRECURSORS FOR SILICA OR METAL SILICATE FILMS

BACKGROUND OF THE INVENTION

Alkoxysilanols are attaining increased attention in the fabrication of electronic devices, where they are reacted with metal containing precursors to deposit films of silicon and metal containing materials. Specifically, as component device (i.e., transistors) size shrinks and increasing densities of component devices and circuits are patterned, traditional silica dielectric insulating materials between those component devices and circuits are inadequate and the industry has sought better dielectric materials deposited at relatively low temperature. Alkoxysilanols reacted with metal containing compounds at temperature below 300° C. have been investigated to achieve the needed low dielectric insulating materials to electrically isolate smaller electronic component devices and circuits having increased densities and smaller overall dimensions.

WO 02/27063 describes alkoxysilanols, such as tris-(tert-butoxy)silanol, for reaction with metals or metalloid containing precursors to deposit metal or metalloid silicate. The alkoxysilanols are generically described as containing: $[(R^1)(R^2)(R^3)Co]-[(R^4)(R^5)(R^6)Co]-[(R^7)(R^8)(R^9)CO]-SiOH$; where R" can be the same or different, n=1–9.

WO 03/083167 also describes alkoxysilanols of the same scope described in WO 02/270063 for reaction with aluminum containing precursors to form silica aluminates.

Backer, et. al., "Esters Mixtes De L'Acide Tetrathio-Orthosilicique", Rec. Trav. Chim., 61, (1942), pp 500–512, describes the synthesis of tris-(butoxy)silanol.

Goedel, et. al., "Hyperbranched Poly(alkoxysilonanes)", Polymer Preprints, 42(1), (2001), pp 242–243, discloses the polymerization of alkoxysilanols, such as tris-(ethoxy)silanol.

Hausman, et. al., "Rapid Vapor Deposition of Highly Conformal Silica Nanoaluminates", Science, Vol. 298, Oct. 11, 2002, pp 402–406, describes the atomic layer deposition (ALD) of tris-(tert-butoxy)silanol and trimethylaluminum in alternating sequence to provide thin films, which can be used in electronic applications.

Muller, Richard, "Zur Darstellung von Alkoxy- und Alkoxysiloxy-silanolen", Z. Chem., 23, Jg. (1983), p 252, identifies various tris-(alkoxy) silanols in its Table 1, last entry, and Table 2, including in the latter; tris-(PhO)silanol.

Schott, et. al., "Alkoxy-silanole—partielle Kieselsaureester", Z. Anorg. Allg. Chemie, 459, (1979), pp 177–186, discloses the synthesis of trialkoxy silanoles and dialkoxy silandioles.

Alkoxysilanols that have been presently contemplated for manufacturing silica-metal films have suffered from undesirable physical properties. To facilitate ease of use, alkoxysilanols should be readily synthesized, available in high purity and exhibit ease of delivery from the site of storage to the site of reaction. The novel alkoxysilanols of the present invention overcome the disadvantages of the prior art and exhibit good properties for manufacturing silica-metal films, as will be demonstrated below.

BRIEF SUMMARY OF THE INVENTION

The present invention is a composition selected from the group consisting of bis(tert-butoxy)(iso-propoxy)silanol, bis(iso-propoxy)(tert-butoxy)silanol, bis(tert-pentoxy)(iso-propoxy)silanol, bis(iso-propoxy)(tert-pentoxy)silanol, bis(tert-pentoxy)(tert-butoxy)silanol, bis(tert-butoxy)(tert-pentoxy) silanol and mixtures thereof; its use to form a metal or metalloid silicate layer on a substrate and the synthesis of the mixed alkoxysilanols.

BRIEF DESCRIPTION OF THE DRAWING

The drawing is a graph of a comparison of the vapor pressure of the prior art alkoxysilanol; tris(tert-pentoxy) silanol (TPOSL) versus the novel mixed alkoxysilanol; bis(tert-butoxy)(isopropoxy)silanol (BTBIPOSL) showing a consistent 10-fold higher vapor pressure for the bis(tert-butoxy)(isopropoxy)silanol over a range of preferred potential operating temperatures for the film deposition process in which the alkoxysilanols would be used.

DETAILED DESCRIPTION OF THE INVENTION

This invention is related to a novel class of mixed alkoxysilanols, their synthesis and use. These mixed alkoxysilanols can be employed as potential precursors to make silica or metal silicates via either the chemical vapor deposition (CVD) or atomic layer deposition (ALD) method at temperatures less than 500° C. These compounds are prepared via reaction of $SiCl_4$ with two equivalents of either bulky alcohols ($HOR^1$), such as tert-butanol or tert-pentanol, in the presence of base or metal alkoxides ($MOR^1$, i.e., metal salt of the alcohol), followed by addition of one equivalent of either less bulky alcohol ($HOR^2$), such as iso-propanol, in the presence of base or the corresponding metal alkoxide ($MOR^2$), then followed by hydrolysis at lower temperature.

The mixed alkoxysilanols are found to be liquid at room temperature and thermally stable. Being liquid and having higher vapor pressure, these new compounds are better precursors, than those commercially available tris(alkoxy) silanols, such as; tris(tert-butoxy)silanol (TBOSL) or tris (tert-pentoxy)silanol (TPOSL), since TBOSL is a solid at room termperature and TPOSL's vapor pressure is very low (~2 torr at 96° C.).

These novel, thermally stable, mixed alkoxysilanols have been prepared as potential precursors for forming low thermal budged metal silicates or silica films. Among the mixed alkoxysilanols, bis(tert-butoxy)(iso-propoxy)silanol is easy to prepare and is possible to make in the high purity required by the semiconductor industry. The vapor pressure of bis (tert-butoxy)(iso-propoxy)silanol was found to be about 10 times higher (see the drawing), than that of tris(tert-pentoxy) silanol (TPOSL), a precursor currently evaluated by the semiconductor industry as a potential source for ALD $SiO_2$, thus making the mixed alkoxysilanols better precursors as CVD or ALD precursors.

Tris(alkoxy)silanol precursors are commercially available. They can be prepared via a two-step procedure, i.e. either equation 1 or equation 2, followed by hydrolysis, as in equation 3.

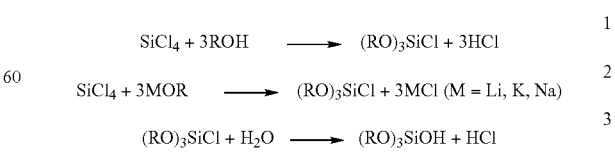

The thermal stability of the tris(alkoxy)silanol is directly related to the alkyl groups. For example, tris(tert-butoxy) silanol and tris(tert-pentoxy)silanol are very stable, whereas tris(iso-propoxy)silanol and tris(ethoxy)silanol are not stable and undergo polymerization to form polysiloxanes upon heating.

The synthesis of mixed alkoxysilanol is more complicated, involving a three-step process as shown in equations 4 to 7.

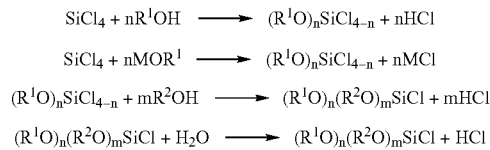

$$SiCl_4 + nR^1OH \longrightarrow (R^1O)_nSiCl_{4-n} + nHCl \quad 4$$

$$SiCl_4 + nMOR^1 \longrightarrow (R^1O)_nSiCl_{4-n} + nMCl \quad 5$$

$$(R^1O)_nSiCl_{4-n} + mR^2OH \longrightarrow (R^1O)_n(R^2O)_mSiCl + mHCl \quad 6$$

$$(R^1O)_n(R^2O)_mSiCl + H_2O \longrightarrow (R^1O)_n(R^2O)_mSiCl + HCl \quad 7$$

where n = 1—2; m = 1—2 and n + m = 3.

In order to make stable mixed alkoxysilanol, it is preferred to choose a bulky alcohol for the first step (equation 4 or 5) to prevent further substitution of chloro ligands, allowing quantitative conversion of $SiCl_4$ into monoalkoxytrichlorosilane or bis(alkoxy)dichlorosilane. If the alkoxy groups are not bulky enough, a mixture of alkoxytrichlorosilane, bis(alkoxy)dichlorosilane and tris(alkoxy)chlorosilane would be generated. Thus, tert-butanol or tert-pentanol is preferred for the first step. Preferably two equivalents of bulky alcohol are used to make bis(alkoxy)dichlorosilane. The distinct alcohol for the second step should also be bulky enough to prevent formation of fully substituted alkoxysilane, but only one equivalent of the second alcohol should be used to avoid full substitution of the silanol.

For example, if two-equivalents of tert-butanol is used in the first step and two equivalents of iso-propanol is employed in the second step, then the undesired bis(tert-butoxy)bis(iso-propoxy)silane is formed. The resulting fully substituted alkoxysilane would be extremely difficult to remove from the final product, mixed alkoxysilanol, as their boiling points are usually too close.

The by-product HCl plays a role in the stability of the resulting mixed alkoxysilanols. There are two ways to remove the generated HCl from the reaction: as organic base salt, such as pyridine.HCl; or as inorganic base. Inorganic base is preferable over organic base, since the organic base can cause problems in the following separation or CVD/ALD process. Reaction temperature is also important in successful synthesis of mixed alkoxysilanols, as higher temperature promotes other reactions, which result in products that will be difficult to separate out later by distillation.

The following examples demonstrate that it is possible to obtain the desirable mixed alkoxysilanols. The actual large scale process to make these compounds can be varied depending on the compound itself.

EXAMPLE 1

Synthesis of bis(iso-propoxy)(tert-pentoxy)silanol 20 g (0.118 mol) of $SiCl_4$ was loaded in a 1000 ml three-neck flask with 500 ml hexanes. The flask was cooled down to –40° C. with a cold bath containing dry ice and iso-propanol. 18 ml (0.237 mol) of iso-propanol and 11.3 ml (0.118 mol) of tert-pentanol were added slowly via addition funnel. The temperature was kept at less than –20° C. 30 ml of pyridine was added to the flask slow to generate a lot of white precipitate which is pyridine.HCl. The cold bath was removed and the flask was stirred for 3 hours. Gas chromatograph/mass spectrometer (GC/MS) measurement of the reaction mixture indicated formation of bis(iso-propoxy)(tert-pentoxy)chlorosilane, plus other products. Filtration and removal of solvents resulted in about 23 g of white slurry. The white slurry was dropwise added to a solution containing 40 ml of ether, 15 ml of water, and 15 ml of pyridine at a temperatue below –20° C. until completion of the addition. The resulting white slurry was stirred for 3 hours. The organic layer was separated and dried over anhydrous $CaCl_2$ for two days. GC/MS indicated formation of bis(iso-propoxy)(tert-pentoxy)silanol (79.5%) as the major product, plus tetrakis(iso-propoxy)silane (2.8%), tris (iso-propoxy)(tert-pentoxy)silane (12.4%), and tris(iso-propoxy)silanol (1.3%). It was very difficult to separate bis(iso-propoxy)(tert-pentoxy)silanol from tris(sio-propoxy)(tert-pentoxy)silane via vacuum distillation. However, it would be possible to purify it if the synthesis was done on a large scale.

EXAMPLE 2

Synthesis of bis(iso-propoxy)(tert-butoxy)silanol 20 g (0.118 mol) of $SiCl_4$ was loaded in a 1000 ml three-neck flask with 500 ml hexane. The flask was cooled down to –40° C. with a cold bath containing dry ice and iso-propanol. 11.3 ml (0.118 mol) of tert-butanol was added slowly via addition funnel. The temperature was kept at less than –20° C. 10 ml of pyridine was added to the flask slowly to generate a lot of white precipitate, which is pyridine.HCl. The cold bath was removed and the flask was stirred for 3 hours. A mixture of 18 ml iso-propanol and 20 ml pyridine were added slowly to the resulting white slurry. The reaction mixture was stirred overnight. GC/MS measurement of the reaction mixture indicated formation of bis(iso-propoxy)(tert-butoxy)chlorosilane and tris(iso-propoxy)(tert-butoxy)silane. Filtration and removal of solvents resulted in white slurry. The white slurry was dropwise added to a solution containing 50 ml of ether, 50 ml of water, and 15 ml of pyridine at temperatue below –20° C. until completion of the addition. The resulting white slurry was stirred for 2 hours. The organic layer was separated and dried over anhydrous $CaCl_2$ for two days. GC/MS indicated formation of bis(iso-propoxy)(tert-butoxy)silanol as the major product (55%), plus tris(sio-propoxy)(tert-butoxy)silane (34%).

EXAMPLE 3

Synthesis of bis(tert-butoxy)(iso-propoxy)silanol 20 g (0.118 mol) of $SiCl_4$ was loaded in a 1000 ml three-neck flask with 400 ml hexane. The flask was cooled down to –40° C. with a cold bath containing dry ice and iso-propanol. 22.6 ml (0.236 mol) of tert-butanol was added slowly via addition funnel. The temperature was kept at less than –20° C. 20 ml of pyridine was added to the flask slowly to generate a lot of white precipitate, which is pyridine.HCl. The cold bath was removed and the flask was stirred overnight after removal of the cold bath. Filtration was applied to give a liquid to which 9 ml (0.118 mol) of iso-propanol was added at temperature below 40° C. 10 ml of pyridine was added slowly to the resulting white slurry. The reaction mixture was stirred for 5 hours after removal of the cold bath. Filtration and removal of solvents resulted in white slurry. The white slurry was dropwise added to a solution containing 50 ml of ether, 50 ml of water, and 15 ml of pyridine at temperatue below –0° C. until completion of the addition. The resulting white slurry was stirred overnight. The organic layer was separated and dried over anhydrous $CaCl_2$ for several days. GC/MS indicated formation of bis(tert-butoxy)(iso-propooxy)silanol as the major product (>80%), plus bis(iso-propoxy)bis(tert-butoxy)silane. Vacuum distillation gave pure bis(tert-butoxy)(iso-propoxy)silanol (~104° C./2 torr). Thermogravimetric analysis/differential scanning calorimetry (TGA/DSC) measurement shows the boiling point is 207° C.

EXAMPLE 4

Synthesis of bis(tert-butoxy)(iso-propoxy)silanol 20 g (0.0799 mol) of bis(tert-butoxy)dichlorosilane prepared by reaction of $SiCl_4$ with two equivalents of tert-butanol in the presence of pyridine was loaded in a 1000 ml three-neck flask with 200 ml hexane. The flask was cooled down to −20° C. with a cold bath containing dry ice and iso-propanol. 4.8 g (0.08 mol) of iso-propanol was added. The temperature was kept at less than −20° C. 6.3 g of pyridine was added to the flask slowly to generate a lot of white precipitate, which is pyridine.HCl. The cold bath was removed and the flask was stirred for several days at room temperature after removal of the cold bath. Filtration and removal of solvents resulted in white slurry. The white slurry was dropwise added to a solution containing 50 ml of ether, 50 ml of water, and 6 g of $NH_4.HCO_3$ at a temperatue below −10° C. until completion of the addition. The resulting white slurry was stirred overnight. The organic layer was separated and dried over anhydrous $CaCl_2$. GC/MS indicated the formation of bis(tert-butoxy)(iso-propooxy)silanol as the major product (93.8%), plus bis(tert-butoxy)(iso-propoxy)chlorosilane. Vacuum distillation gives pure bis(tert-butoxy)(iso-propoxy)silanol (~104° C./2 torr).

Being liquid and having higher vapor pressure, these new mixed alkoxysilanols are better precursors than those commercially available tris(alkoxy)silanols, such as; tris(tert-butoxy)silanol (TBOSL) or tris(tert-pentoxy)silanol (TPOSL), since TBOSL is a solid at room termperature and TPOSL's vapor pressure is very low (~2 torr at 96 C).

The novel mixed alkoxysilanols may be used advantageously in a method for forming a metal or metalloid silicate on a substrate, such as a dielectric layer in an electronic device fabrication of solid state transistors, capacitors, vias, and circuits in general by contacting a metal or metalloid containing compound with a mixed alkoxysilanol selected from the group consisting of bis(tert-butoxy)(iso-propoxy)silanol, bis(iso-propoxy)(tert-butoxy)silanol, bis(tert-pentoxy)(iso-propoxy)silanol, bis(isopropoxy)(tert-pentoxy)silanol, bis(tert-pentoxy)(tert-butoxy)silanol, bis(tert-butoxy)(tert-pentoxy)silanol and mixtures thereof and reacting the metal or metalloid containing compound with the mixed alkoxysilanol to form the metal or metalloid silicate on the substrate. Preferably, the mixed alkoxysilanols and the metal or metalloid containing compounds are each made available in the liquid state to ease transport to the reaction chamber or tool where they are blended and reacted, and they are both preferably vaporized in that reaction chamber or tool at low temperatures to maintain the thermal budget of the electronic device being fabricated. Typically, the metal or metalloid is selected from the group consisting of titanium, hafnium, zirconium, yttrium, lanthanum, scandium, magnesium, boron, aluminum and mixtures thereof. The ligand which is used to make the metal or metalloid compound could be amides, alkyls, alkoxides, halides and mixtures thereof.

The present invention has been described with regard to several preferred embodiments, however, the full scope of the present invention should be ascertained from the claims which follow.

What is claimed is:

1. A composition selected from the group consisting of bis(tert-butoxy)(iso-propoxy)silanol, bis(iso-propoxy)(tert-butoxy)silanol, bis(tert-pentoxy)(iso-propoxy)silanol, bis(iso-propoxy)(tert-pentoxy)silanol, bis(tert-pentoxy)(tert-butoxy)silanol, bis(tert-butoxy)(tert-pentoxy)silanol and mixtures thereof.

2. The invention of claim 1 wherein the composition is bis(iso-propoxy)(tert-butoxy)silanol.

3. The invention of claim 1 wherein the composition is bis(tert-pentoxy)(iso-propoxy)silanol.

4. The invention of claim 1 wherein the composition is bis(iso-propoxy)(tert-pentoxy)silanol.

5. The invention of claim 1 wherein the composition is bis(tert-pentoxy)(tert-butoxy)silanol.

6. The invention of claim 1 wherein the composition is bis(tert-butoxy)(tert-pentoxy)silanol.

7. Bis(tert-butoxy)(iso-propoxy)silanol.

8. A method for forming a metal or metalloid silicate on a substrate, comprising contacting a metal or metalloid containing compound with a mixed alkoxysilanol selected from the group consisting of bis(tert-butoxy)(iso-propoxy)silanol, bis(iso-propoxy)(tert-butoxy)silanol, bis(tert-pentoxy)(iso-propoxy)silanol, bis(iso-propoxy)(tert-pentoxy)silanol, bis(tert-pentoxy)(tert-butoxy)silanol, bis(tert-butoxy)(tert-pentoxy)silanol and mixtures thereof and reacting the metal or metalloid containing compound with the mixed alkoxysilanol to form the metal or metalloid silicate on the substrate.

9. The method of claim 8 wherein the metal or metalloid containing compound is in the vapor state during reaction.

10. The method of claim 8 wherein the mixed alkoxysilanol is in the vapor state during reaction.

11. The method of claim 8 wherein the mixed alkoxysilanol is bis(tert-butoxy)(iso-propoxy)silanol.

12. The method of claim 8 wherein the metal or metalloid is selected from the group consisting of titanium, hafnium, zirconium, yttrium, lanthanum, scandium magnesium, boron, aluminum and mixtures thereof.

13. The method of claim 12 wherein the metal or metalloid containing compound is selected from metal amides, metal alkoxides, metal hydrides, metal alkyls and mixtures thereof.

14. A method for forming a metal or metalloid silicate on a substrate, comprising contacting a metal or metalloid containing compound with bis(tert-butoxy)(iso-propoxy)silanol and reacting the metal or metalloid containing compound with the bis(tert-butoxy)(iso-propoxy)silanol to form the metal or metalloid silicate on the substrate.

* * * * *